United States Patent [19]
Zembrodt

[11] Patent Number: 6,120,737
[45] Date of Patent: Sep. 19, 2000

[54] FRAGRANT LIGHT BULB RING

[75] Inventor: Anthony R. Zembrodt, Covington, Ky.

[73] Assignee: Bath & Body Works, Inc., Reynoldsburg, Ohio

[21] Appl. No.: 09/185,861

[22] Filed: Nov. 4, 1998

[51] Int. Cl.[7] ....................................................... A62B 7/08

[52] U.S. Cl. ........................ 422/122; 106/243; 313/315; 422/123; 422/125

[58] Field of Search ................................... 422/125, 122, 422/123; 313/315; 106/243; 392/393

[56] References Cited

U.S. PATENT DOCUMENTS

| | | | |
|---|---|---|---|
| 4,892,711 | 1/1990 | Tendick, Sr. | 422/125 |
| 5,911,955 | 6/1999 | Fullam | 422/125 |

*Primary Examiner*—Krisanne Thornton
*Attorney, Agent, or Firm*—Colucci & Umans

[57] ABSTRACT

An arrangement is used with a light bulb for emitting fragrance. The arrangement has a ring or other shaped member made of a first polymer. The first polymer has a first low melting point which is about a first temperature at a spaced location from the surface of the light bulb when it is lit. A volatilizable fragrance is combined with the first polymer for being volatilized from the first polymer when the ring member is exposed to the first temperature. A plurality of feet extend inwardly of the ring member for engaging the surface of a light bulb to maintain the ring member at the spaced location on the light bulb. These spacer feet are made of a second polymer having a second high melting point compared to the first low melting point. The second melting point is above a second temperature at the surface of the light bulb when it is lit.

6 Claims, 2 Drawing Sheets

FRAGRANT LIGHT BULB RING

FIELD AND BACKGROUND OF THE INVENTION

The present invention relates in general to room fresheners, and in particular to a new and useful ring meant to be engaged around a light bulb and which gives off fragrance to the room when heated by the heat from the light bulb.

The light bulb ring must be made of special material to avoid problems associated with the high temperatures of the light bulb.

In the past other products meant to engage a light bulb were made of ceramic or plaster pieces, or even absorbent material like asbestos and cellulose. The problem with these is that the ceramic and plaster can break easily if they fall from the light bulb and, importantly, the consumers had to add messy perfume oil to the plaster every time they wanted to fragrance the room.

Similar problems occurred when materials like asbestos or cellulose were used. Although this avoided the breakage problem, the consumer still had to add oil each time they wanted to use the product. The use of asbestos also poses other safety problems.

U.S. Pat. No. 4,184,099, which is incorporated here by reference, discloses a polymer composition which releases fragrance when it comes into direct contact with a light bulb heat. Either high melting polymers with poor fragrance containing and releasing characteristics must be used or the polymers will melt on the lit light bulb.

A need remains, however, for a room freshener of this type which is effective and safe.

SUMMARY OF THE INVENTION

The present invention addresses both problems of the prior art (breakage and messy oil application) and provides a decorative, colored product that lasts for up to 30 days.

The solution is to use polymers to carry the oil and dispense the perfume. Although fragranced polymers are well known in the industry, they are not used because, inter alia, they melt if placed on a burning light bulb. Those polymers that do not melt cannot carry and release the fragrance as readily or are as cost effective. These problems were avoided by judiciously selecting thermally stable polymers to act as the body and feet to keep the body of the fragranced polymer away from the direct heat of the light bulb.

The temperature near a light bulb is a function of the distance from the bulb. Knowing the temperature the polymer would experience at a certain distance from the burning light bulb, specific polymers (with the highest melt temperatures) were selected.

Polyolefins are preferred because they can release perfumes more readily than other polymers. High melt temperature polymers, such as Thermx and Rynite (trademarks), that come in direct contact with the bulb are also used.

Three small feet acting like tooth picks stuck into the inside surface of the fragranced polymers are positioned inside the ring which allows the ring to sit on the bulb at a spaced location. To aid in manufacture, a special machine was developed to insert the feet immediately after the ring was injection molded. Thus, the solidifying polymer was able to secure itself around the feet and make a strong bond to keep the feet from falling out.

In this way one can position the light bulb ring on top of a light bulb. The feet keep the fragranced polymer away from the direct heat of the bulb and the heat of the bulb allows the fragrance to be released at a rate great enough to fragrance an entire room. Testing has shown that the invention can fragrance a room for about one month.

Accordingly, an object of the present invention is to provide a fragrance emitting arrangement for use with a light bulb, which comprises a ring or other shaped spaced member made of a first polymer, the polymer having a relatively low melting point which is above a temperature at a spaced location from the surface of the light bulb when it is lit, a volatilizable fragrance combined with the first polymer for being volatilized from the first polymer when the ring member is exposed to the first temperature, and spacer means connected to the ring member for engaging the surface of a light bulb to maintain the ring member at the spaced location on the light bulb, the spacer means being made of a second polymer having a second high melting point compared to the first relatively low melting point, the second melting point being above a second temperature at the surface of the light bulb when it is lit.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 4:
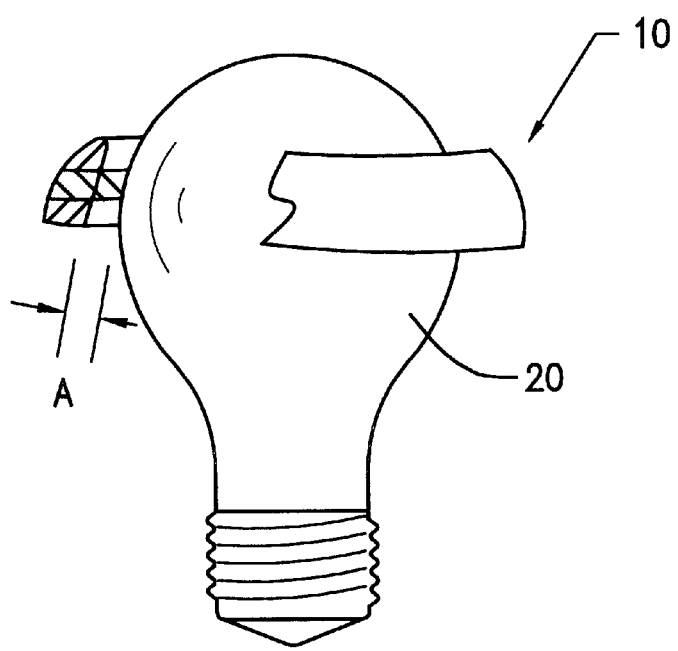
FIG. 4 is a side elevational view thereof, partly in section, showing the arrangement engaged to a light bulb.

Referring to the figures in which a preferred embodiment of the invention is disclosed, the present invention is a fragrance emitting ring arrangement generally designated 10, for use with a light bulb 20. The arrangement comprises a ring member 12 made of a first polymer, the first polymer having a first relatively low melting point which is about a first temperature at a spaced location from the surface of the light bulb when the bulb is lit. The spacing, show at A in FIG. 4, is preferably about 5/16 inch and may be about ¼ to 1¼ inches. The first temperature is about 200° F. and usually from about 180° to 240° F. or 250° F. for standard lit incandescent electric light bulbs of 40 to 100 watts output. A volatilizable fragrance such as fragrance oil is combined with the first polymer for being volatilized from the first polymer when the ring member is exposed to the first temperature.

Spacer means for maintaining the spacing S, are connected to the ring member for engaging the surface of the light bulb to maintain the ring member at the spaced location and on or around a portion of the light bulb as shown in FIG. 4. The spacer means are, for example, three or more spacer feet 14, circumferentially spaced around the inner surface of the ring member. The feet 14 are each made of a second polymer having a second, high melting point compared to the first low melting point, the second melting point being above a second temperature at the surface of the light bulb when it is lit which can be as high as 700° F. but usually about 450° F. to 550° F.

Figure 1:
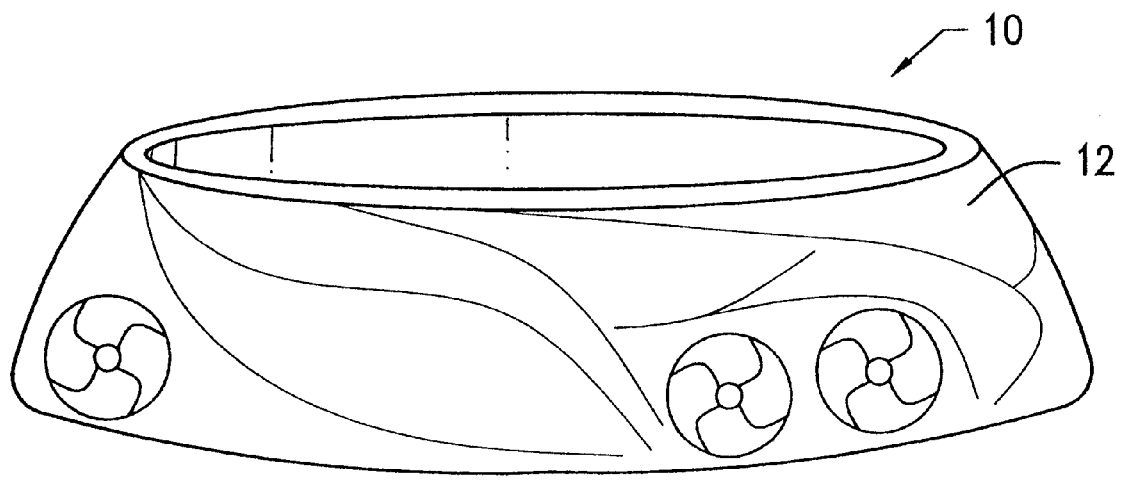
FIG. 1 is a perspective view of the fragrant light bulb ring arrangement of the present invention.
Figure 2:
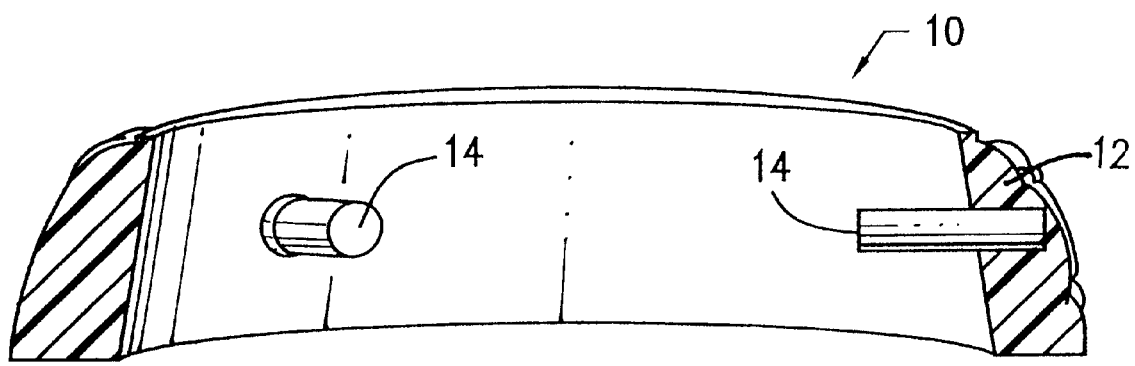
FIG. 2 is a sectional view thereof.
Figure 3:
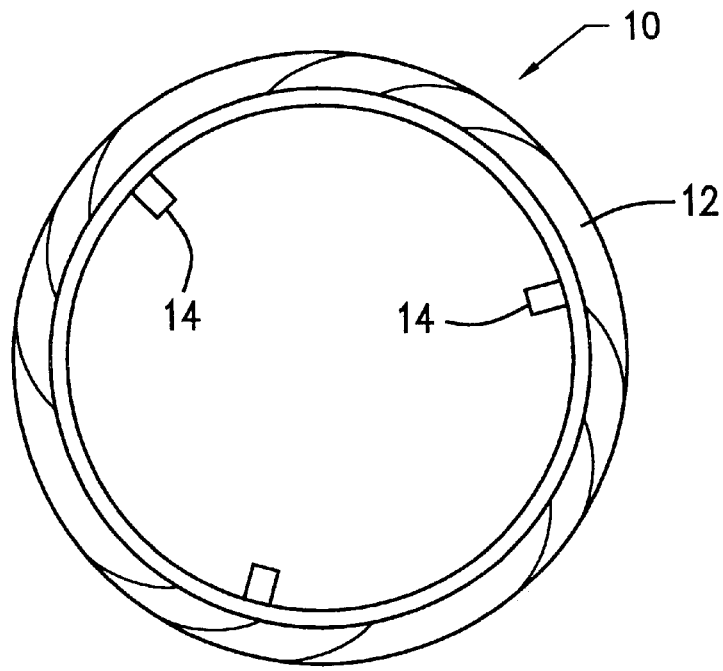
FIG. 3 is a top plane view thereof.

The outer diameter of the ring member as shown in FIG. 2 is typically about 3½ inches, but can be anywhere from 2½ to 4½ inches. Conventional harps which hold a lamp shade in place help dictate the optimum distance. Each of the feet made of the second polymer 14 are inserted into the body of the ring member 12 and extends radially inwardly for touching the outer surface of a bulb as shown in FIG. 4. This can be done by pressing each foot into the member while it is still soft just after it is formed, e.g. by injection molding.

High temperature-resistant Thermx or Rynite can be used for the feet 14 while absorbent, but relatively low temperature polyolefins, such as polypropylene, is used for the ring member 12. Since polymers are generally poor conductors of heat, heat from the light bulb 20 does not convey along the feet 14 to the lower temperature polymer 12 and, thus, does not cause melting of the polymer as long as the spacing is maintained away from the outer surface of the bulb. The heat, however, is instrumental in causing the fragrance, which is interspersed in the polymer of ring member 12, to evaporate and be emitted to the room.

One way of incorporating the fragrance into the first polymer is to select thermoplastic as the first polymer and, when the first polymer is melted, mix the fragrance with the first polymer and then allow it to cool, for example, at the end of an injection molding process, to form the ring member.

Thermx and Rynite are trademarks for polyesters like polyethylene terphthalate or polybutylene terphthalate. These polymers can also be glass filled for added stability.

Thermx and Rynite melt at about 475° to 525° F.

The temperature which an object will attain if placed about ⅝ inch away from a 100 watt light bulb is about 248° to 266° F. (120° to 130° C.). Polymers with a melt temperature above 266° F. (130° C.) can be chosen for the ring because they will not melt at this point. Polymers which fit this criteria are polypropylene, polyamides, such as nylons, rubbers, polycarbonates, PET PTFE, PVDF and many other custom and commercial materials. Polypropylene is preferred because it has good release characteristics for the perfume and it has a melt temperature about 329° F. (165° C.).

Perfumes can be loaded into the low melting point polymer from 1 to 50 percent by weight. The preferred level is the highest level possible for the polymer being used to minimize costs in manufacture. For polypropylene, the polymer of choice, the perfume is loaded with 25 percent perfume. The actual level of perfume will be dictated by intensity performance in the room.

For the feet the polymer must be able to withstand a temperature of about 500° to 536° F. (260° to 280° C.). Various polymers which have this melt point criteria can be used as the feet.

Rynite and Thermx are two of the possible choices as noted above. Thermx is preferred.

The person with ordinary skill in this art can select from a wide variety of polymers for the ring member and feet, within the scope of this invention. The ring should use a polymer having a melting point above about 250° F. and below about 430° F. and the feet should use a polymer having a melting point above about 450° F.

Although a ring member 12 is illustrated, the member may be an open or closed loop and any shape such as triangular, square or other polygonal shape or oval, for example, or even other shapes to be spaced from the bulb.

While a specific embodiment of the invention has been shown and described in detail to illustrate the application of the principles of the invention, it will be understood that the invention may be embodied otherwise without departing from such principles.

What is claimed is:

1. A fragrance emitting arrangement for use with a light bulb, comprising:

a spaced member made of a first polymer, the first polymer having a first relatively low melting point which is about a first temperature at a spaced location from the surface of the light bulb when the light bulb is lit;

a volatilizable fragrance combined with the first polymer for being volatilized from the first polymer when the spaced member is exposed to the first temperature; and a plurality of feet extending radially inwardly from an inner surface of the spaced member for engaging the surface of a light bulb to maintain the spaced member at the spaced location on the light bulb, the feet each being made of a second polymer which is different for the first polymer, the second polymer having a second relatively high melting point compared to the first low melting point, the second melting point being above a second temperature at the surface of the light bulb when it is lit, the feet also extending radially outwardly into the spaced member for connecting the feet to the spaced member and for supporting the spaced member.

2. An arrangement according to claim 1 wherein the first polymer is a polyolefin, and the second polymer is a high melt temperature polymer which melts at above about 450° F.

3. An arrangement according to claim 2 wherein the polyolefin has a melting point between about 250° F. and 430° F.

4. An arrangement according to claim 1 wherein the feet have means are selected to maintain a spacing between the outer surface of the bulb and any part of the spaced member of between about ¼ and 1¼ inches.

5. An arrangement according to claim 4 wherein the spaced member is a ring member.

6. An arrangement according to claim 1 wherein the spaced member is a ring member.

* * * * *